US012108980B2

(12) United States Patent
Hancock et al.

(10) Patent No.: US 12,108,980 B2
(45) Date of Patent: Oct. 8, 2024

(54) ELECTROSURGICAL INSTRUMENT FOR ABLATION AND RESECTION

(71) Applicant: CREO MEDICAL LIMITED, Monmouthshire (GB)

(72) Inventors: Christopher Paul Hancock, Bath (GB); Malcolm White, Chepstow (GB); Patrick Burn, Chepstow (GB); Peter Clegg, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 421 days.

(21) Appl. No.: 16/610,463

(22) PCT Filed: Jun. 1, 2018

(86) PCT No.: PCT/EP2018/064466
§ 371 (c)(1),
(2) Date: Nov. 1, 2019

(87) PCT Pub. No.: WO2018/220178
PCT Pub. Date: Dec. 6, 2018

(65) Prior Publication Data
US 2020/0289195 A1    Sep. 17, 2020

(30) Foreign Application Priority Data

Jun. 1, 2017  (GB) ..................... 1708726

(51) Int. Cl.
*A61B 18/14*       (2006.01)
*A61B 18/00*       (2006.01)
(Continued)

(52) U.S. Cl.
CPC ...... *A61B 18/1492* (2013.01); *A61B 18/1206* (2013.01); *A61B 18/1815* (2013.01);
(Continued)

(58) Field of Classification Search
CPC ........ A61B 18/1815; A61B 2018/1823; A61B 18/1206; A61B 18/12; A61B 18/16;
(Continued)

(56) References Cited

U.S. PATENT DOCUMENTS 5,057,106 A * 10/1991 Kasevich ........... A61B 18/1815
                                                  600/549
6,231,571 B1 * 5/2001 Ellman ............... A61B 18/1482
                                                  606/49
(Continued)

FOREIGN PATENT DOCUMENTS

EP    2716251 A1    4/2014
GB    2531434 A  *  4/2016 ............ A61B 18/12

OTHER PUBLICATIONS

International Search Report and Written Opinion, issued by International Searching Authority in corresponding International Application No. PCT/EP2018/064466, mailed on Oct. 5, 2018.
(Continued)

*Primary Examiner* — Khadijeh A Vahdat
*Assistant Examiner* — Marina Delaney Templeton
(74) *Attorney, Agent, or Firm* — ArentFox Schiff LLP

(57) ABSTRACT

An electrosurgical instrument which is capable of simultaneously ablating an area of tissue with microwave energy and performing resection with RF energy. The instrument comprises a structure for conveying both RF and microwave energy to an instrument tip that is configured to emit the microwave energy in a manner suitable for ablation (e.g. as a substantially spherical field) and to emit the RF energy in a more focussed manner to enable accurate and controllable resection to be performed. The energy conveying structure comprises a coaxial transmission line for conveying microwave energy. The coaxial transmission line has a hollow
(Continued)

inner conductor that defines a passage that supports a second transmission line for conveying radiofrequency energy.

16 Claims, 3 Drawing Sheets

(51) Int. Cl.
  *A61B 18/12* (2006.01)
  *A61B 18/16* (2006.01)
  *A61B 18/18* (2006.01)
(52) U.S. Cl.
  CPC ........... *A61B 2018/00077* (2013.01); *A61B 2018/00083* (2013.01); *A61B 2018/00577* (2013.01); *A61B 2018/00601* (2013.01); *A61B 2018/00994* (2013.01); *A61B 2018/1417* (2013.01); *A61B 2018/162* (2013.01); *A61B 2018/1861* (2013.01); *A61B 2218/001* (2013.01)
(58) Field of Classification Search
  CPC ... A61B 18/1492; A61B 18/14; A61B 18/082; A61B 2018/00577; A61B 2018/1876; A61B 2018/128; A61B 2018/1417; A61B 2018/00071; A61B 2018/00077; A61B 2018/126; A61B 2018/1838; A61B 2018/00994; A61B 2018/00601; A61B 2018/00083
  See application file for complete search history.

(56) References Cited

U.S. PATENT DOCUMENTS

| | | | | |
|---|---|---|---|---|
| 8,317,782 | B1* | 11/2012 | Ellman | A61B 18/14 |
| | | | | 606/41 |
| 11,234,761 | B2* | 2/2022 | Leung | A61B 18/1492 |
| 2002/0077626 | A1* | 6/2002 | Ellman | A61B 18/1482 |
| | | | | 606/41 |
| 2008/0015570 | A1* | 1/2008 | Ormsby | A61B 18/1492 |
| | | | | 606/41 |
| 2010/0045558 | A1* | 2/2010 | Rossetto | A61B 18/18 |
| | | | | 343/790 |
| 2011/0130750 | A1* | 6/2011 | Ormsby | A61B 18/18 |
| | | | | 606/33 |
| 2013/0289557 | A1* | 10/2013 | Hancock | H01Q 13/08 |
| | | | | 606/33 |
| 2015/0080891 | A1* | 3/2015 | Shelton, IV | A61B 18/12 |
| | | | | 606/48 |
| 2015/0133910 | A1* | 5/2015 | Brannan | A61B 18/1815 |
| | | | | 606/33 |

OTHER PUBLICATIONS

Search Report under Section 17(5), issued in counterpart British Patent Application No. GB1708726.3, dated Nov. 17, 2017.
Search Report under Section 17(6), issued in counterpart British Patent Application No. GB1708726.3, dated May 4, 2018.

* cited by examiner

ELECTROSURGICAL INSTRUMENT FOR ABLATION AND RESECTION

CROSS-REFERENCE TO RELATED APPLICATIONS

This application is a is a National Stage entry of International Application No PCT/EP2018/064466, filed Jun. 1, 2018, which claims priority to British Patent Application No. 1708726.3, filed Jun. 1, 2017. The disclosures of the priority applications are hereby incorporated in their entirety by reference.

FIELD OF THE INVENTION

The invention relates to a combined ablation and resection instrument, and an energy delivery system to enable ablation and resection by the instrument.

BACKGROUND TO THE INVENTION

Surgical resection is a means of removing sections of unwanted tissue associated with organs within the human or animal body, such as the liver or the spleen or the bowel. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting.

For example, the Hemostatix® Thermal Scalpel System combines a sharp blade with a haemostatic system. The blade is coated with a plastic material and connected to a heating unit which accurately controls the temperature of the blade. The intention is for the heated blade to cauterise the tissue as it is cut.

Other known devices that cut and stop bleeding at the same time do not use a blade. Some devices use radiofrequency (RF) energy to cut and/or coagulate tissue. Other devices (known as harmonic scalpels) use a rapidly vibrating tip to cut tissue.

The method of cutting using RF energy operates using the principle that as an electric current passes through a tissue matrix (aided by the ionic contents of the cells), the impedance to the flow of electrons across the tissue generates heat. When a pure sine wave is applied to the tissue matrix, enough heat is generated within the cells to vaporise the water content of the tissue. There is thus a huge rise in the internal pressure of the cell that cannot be controlled by the cell membrane, resulting in the cell rupturing. When this occurs over a wide area it can be seen that tissue has been transected.

RF coagulation operates by applying a less efficient waveform to the tissue, whereby instead of being vaporised, the cell contents are heated to around 65° C. This dries out the tissue by desiccation and also denatures the proteins in the walls of vessels and the collagen that makes up the cell wall. Denaturing the proteins acts as a stimulus to the coagulation cascade, so clotting is enhanced. At the same time the collagen in the wall is denatured from a rod like molecule to a coil, which causes the vessel to contract and reduce in size, giving the clot an anchor point, and a smaller area to plug.

The application of heat energy to biological tissue is also an effective method of killing cells. For example, the application of microwaves can heat and thus ablate (destroy) biological tissue. This method may in particular be used for the treatment of cancer as the cancerous tissue can be ablated in this way.

SUMMARY OF THE INVENTION

At its most general, the present invention provides an electrosurgical instrument which is capable of simultaneously ablating an area of tissue with microwave energy and performing resection with RF energy. In particular, the invention is concerned with structure for conveying both RF and microwave energy to an instrument tip that is configured to emit the microwave energy in a manner suitable for ablation (e.g. as a substantially spherical field) and to emit the RF energy in a more focussed manner to enable accurate and controllable resection to be performed.

According to a first aspect of the invention, there is provided an electrosurgical instrument for delivering radiofrequency (RF) electromagnetic (EM) energy and microwave EM energy for resection and ablation of biological tissue, the instrument comprising: an energy conveying cable structure comprising: a coaxial transmission line for conveying microwave energy, the coaxial transmission line comprising an inner conductive layer, an outer conductive layer and a dielectric layer separating the inner conductive layer from the outer conductive layer, wherein the inner conductive layer is formed around a hollow longitudinal passage along the cable structure; and a transmission line for conveying radiofrequency energy along the hollow longitudinal passage; and an instrument tip at a distal end of the energy conveying cable structure, the instrument tip comprising: a dielectric tip element extending longitudinally beyond a distal end of the outer conductor, wherein the inner conductor extends longitudinally beyond the distal end of the outer conductor within the dielectric tip element to form a microwave radiator; and an active electrode and a return electrode mounted at a distal end of the dielectric tip, wherein the active electrode and the return electrode are connected to the transmission line to support an RF field therebetween at the distal end of the dielectric tip element. In this aspect of the invention, there are two transmission line structures for the RF energy and microwave energy, which respectively terminate at different energy delivery structures that provide the desired effect.

The coaxial transmission line for conveying the microwave energy may be a first coaxial transmission line, and the transmission line for conveying the radiofrequency energy may be a second coaxial transmission line. The second coaxial transmission line may comprise an innermost conductive element extending through the longitudinal passage, the inner conductive layer, and an innermost dielectric layer separating the inner conductive layer from the innermost conductive element. In this arrangement, the active electrode may be electrically connected to the inner conductive layer and the return electrode may be electrically connected to the innermost conductive element. The innermost conductive element and the outer conductive layer may be electrically grounded. Thus, at the distal end of the energy conveying structure, ablation may be carried out by microwave energy delivered by the inner conductive layer and the outer conductive layer. RF cutting/resection may be performed using energy delivered between the innermost conductive element and the inner conductive layer.

The transmission lines may be provided by a triaxial structure that comprises three conductive elements separated by dielectric layers. The innermost and outermost conductive layers are grounded, while the intermediate (inner) conductive layer is the signal conductor for each transmission line.

In another example, the transmission line for conveying the RF may be wholly contained within the hollow longitudinal passage. For example, the transmission line for conveying the radiofrequency energy may be a pair of wires extending through the hollow longitudinal passage. The pair of wires may be encased in an electrically insulating sheath, e.g. to ensure isolation from the inner conductor.

The energy conveying cable structure may be insertable through a flexible insertion tube of a surgical scoping device (e.g. endoscope, bronchoscope, gastroscope, laparoscope or the like). In particular, the triaxial layered structure may be insertable in an instrument channel of such a scoping device. The energy conveying cable structure may thus be dimensioned to fit in an instrument channel. For example, it may have an outer diameter equal to or less than 3 mm.

The first coaxial transmission line may be arranged to carry microwave energy. To minimise losses, it is desirable for the microwave energy to be carried by a coaxial transmission line having a larger diameter.

The second coaxial transmission line may be arranged to carry the RF energy. Accordingly, the inner conductor forms a first (active) pole of an RF-carrying bipolar transmission line, and the innermost conductive element forms a second (return) pole of the RF-carrying bipolar transmission line.

The innermost conductive element may be a conductive wire or rod. Alternatively or additionally, the innermost conductive element may be integrated with another component that passes through the instrument channel. For example, a tube used to supply liquid or gas to the distal end of the energy conveying structure, or a housing for a control wire, e.g. a guide- or pull-wire, may be formed of, or coated with, a conducting material and may act as the innermost conductive element.

In the present invention, it may be necessary to provide a configuration, such as a diplexer, at the distal end of the energy conveying structure to prevent the higher voltage radiofrequency signal from travelling back along the outer conductive layer, and/or to prevent the microwave signal from travelling back along the innermost conductive element. Additionally or alternatively, a diplexer may be provided at the proximal end of the energy conveying structure to ensure that the RF and microwave energy are split into the RF and microwave channels.

The inner dielectric layer and/or the outer dielectric layer may each comprise a solid tube of dielectric material or a tube of dielectric material having a porous structure. Being a solid tube of dielectric material may mean that the dielectric material is substantially homogeneous. Having a porous structure may means that the dielectric material is substantially inhomogeneous, with a significant number or amount of air pockets or voids. For example, a porous structure may mean a honeycomb structure, a mesh structure, or a foam structure. The dielectric material may comprise PTFE, or another low-loss microwave dielectric. The dielectric material may comprise a tube with a wall thickness of at least 0.2 mm, preferably at least 0.3 mm, more preferably at least 0.4 mm, e.g. between 0.3 and 0.6 mm.

The inner conductive layer and/or the outer conductive layer may comprise: a metal coating on the inside or outside of a tube of material; a solid tube of metal positioned against the inside or outside of a tube of material; or a layer of braided conductive material embedded in a tube of material. The inner conductive layer and/or the outer conductive layer may comprise a silver coating. The inner conductive layer and/or the outer conductive layer may have a thickness of approximately 0.01 mm.

In one configuration the energy conveying structure may be fabricated as a plurality of layers, e.g. a hollow inner tubular layer (the inner dielectric layer); a layer of conductive material on an outer surface of the hollow inner tubular layer (inner conductive layer); a tube of dielectric material on an outer surface of the conductive material (dielectric layer; and a layer of conductive material on an outer surface of the tube of the dielectric material (outer conductive layer). The innermost conductive element may be a rod or wire or conductive material which passes through the hollow inner tubular layer. In some embodiments, the inner dielectric layer may be formed over the innermost conductive element. The structure may, or may not, comprise air gaps between some or all of these layers. An advantage of avoiding air gaps is that losses in the cable may be minimised. In one example, this structure could be manufactured by sequentially coating each subsequent layer over the preceding (inner) layer. Alternatively, this structure could be made by forming one or more of the layers as a first part and one or more of the layers as a second part, and then sliding one part inside of the other. The hollow inner tubular layer preferably comprises polyimide, but may be PTFE or other suitable insulating material. The hollow inner tubular layer may have a thickness of 0.1 mm.

Herein, the term "inner" means radially closer to the centre (e.g. axis) of the layered structure. The term "outer" means radially further from the centre (axis) of the layered structure.

The term "conductive" is used herein to mean electrically conductive, unless the context dictates otherwise.

Herein, the terms "proximal" and "distal" refer to the ends of the energy conveying structure further from and closer to the treatment site, respectively. Thus, in use the proximal end is closer to a generator for providing the RF and/or microwave energy, whereas the distal end is closer to the treatment site, i.e. the patient.

At the distal end of the energy conveying structure, the instrument tip may be collinearly affixed to the outer dielectric layer such that the instrument channel extends through the radiator tip. In other words, the longitudinal passage extends through the dielectric tip element to provide a fluid flow path through the instrument.

Preferably, the radiator tip may have the same inner and outer dimensions as the outer dielectric layer. The dielectric tip element may be made of a ceramic material. The innermost conductive element, inner dielectric layer, and inner conductive layer may extend through the radiator tip. In this way, the radiator tip may provide a microwave radiator at the distal end of the energy conveying structure. RF cutting may also take place at the end of the radiator tip in a region between the innermost conductive element and inner conductive layer. The radiator tip may be configured to radiate microwave energy in a spherical pattern, for example to produce a spherical ablation region. In some embodiments, an arcuate portion of the radiator tip is exposed to the instrument channel. For example, the inner dielectric and the inner conductor may not extend completely through the radiator tip. Preferably, the distalmost end of the innermost conductive element is staggered such that it is in contact with the exposed sector of radiator tip. In this way, when RF energy is conveyed through the energy conveying structure, RF cutting or resection may take place in a region between the innermost conductive element and the inner conductor.

The instrument may form part of an electrosurgical apparatus comprising an electrosurgical generator arranged to supply RF EM energy and microwave EM energy. In this apparatus, the instrument is connected to the generator in a manner whereby the energy conveying cable structure is arranged to convey microwave EM energy via the first coaxial transmission line and RF energy via the second coaxial transmission line.

According to a second aspect of the invention, there is provided an electrosurgical instrument for delivering radiofrequency (RF) electromagnetic (EM) energy and microwave EM energy for resection and ablation of biological tissue, the instrument comprising: a coaxial transmission line for conveying the RF EM energy and the microwave EM energy, the coaxial transmission line comprising an inner conductive layer, an outer conductive layer and a dielectric layer separating the inner conductive layer from the outer conductive layer; and a ball-shaped instrument tip at a distal end of the energy conveying cable structure, the instrument tip comprising: a first conductive hemisphere electrically connected to the inner conductive layer; a second conductive hemisphere electrically connected to the outer conductive layer; and a planar dielectric layer located in a physical separation gap between the first conductive hemisphere and the second conductive hemisphere, wherein the first conductive hemisphere and the second conductive hemisphere are configured to: radiate the microwave EM energy as a substantially spherical field, and provide respectively an active electrode and a return electrode on opposing sides of the separation gap for delivering the RF EM energy. This aspect of the invention utilises how the ball-shaped instrument tip "appears" differently to the microwave energy and RF energy. For the microwave energy it appears as a continuous conductive ball for emitted a spherical field. For the RF energy it appears as a parallel plate capacitor, where the electric field emitted around the edge of the gap between the hemispheres can be used to resect biological tissue. Cutting and resection may therefore be controllable by a user, for example by pull- or guide-wires attached to the instrument tip.

Although the instrument tip is ball-shaped in this aspect, the tip can have different shapes according to the resulting field shape that is desired.

The instrument may be insertable through an instrument channel of a surgical scoping device. For example, the ball-shaped instrument tip may have a diameter equal to or less than 3 mm.

The first conductive hemisphere and the second conductive hemisphere may be symmetrically mounted on the planar dielectric layer. They may be connected to the coaxial transmission line via intermediate connectors. For example, the instrument may include a first electrical connector mounted on a first surface of the planar dielectric layer, the first electrical connector electrically connecting the inner conductive layer to the first conductive hemisphere. The instrument may further comprise a second electrical connector mounted on a second surface of the planar dielectric layer opposite to the first surface, the second electrical connector electrically connecting the outer conductive layer to the second conductive hemisphere.

The coaxial transmission line may include a fluid flow passage for conveying a fluid to the instrument tip. The instrument tip may include a fluid flow outlet connected to the fluid flow passage. The fluid flow passage may extend through the planar dielectric layer.

BRIEF DESCRIPTION OF THE DRAWINGS

Embodiments of the invention will now be described by way of example with reference to the accompanying drawings in which.

DETAILED DESCRIPTION; FURTHER OPTIONS AND PREFERENCES

Figure 1:
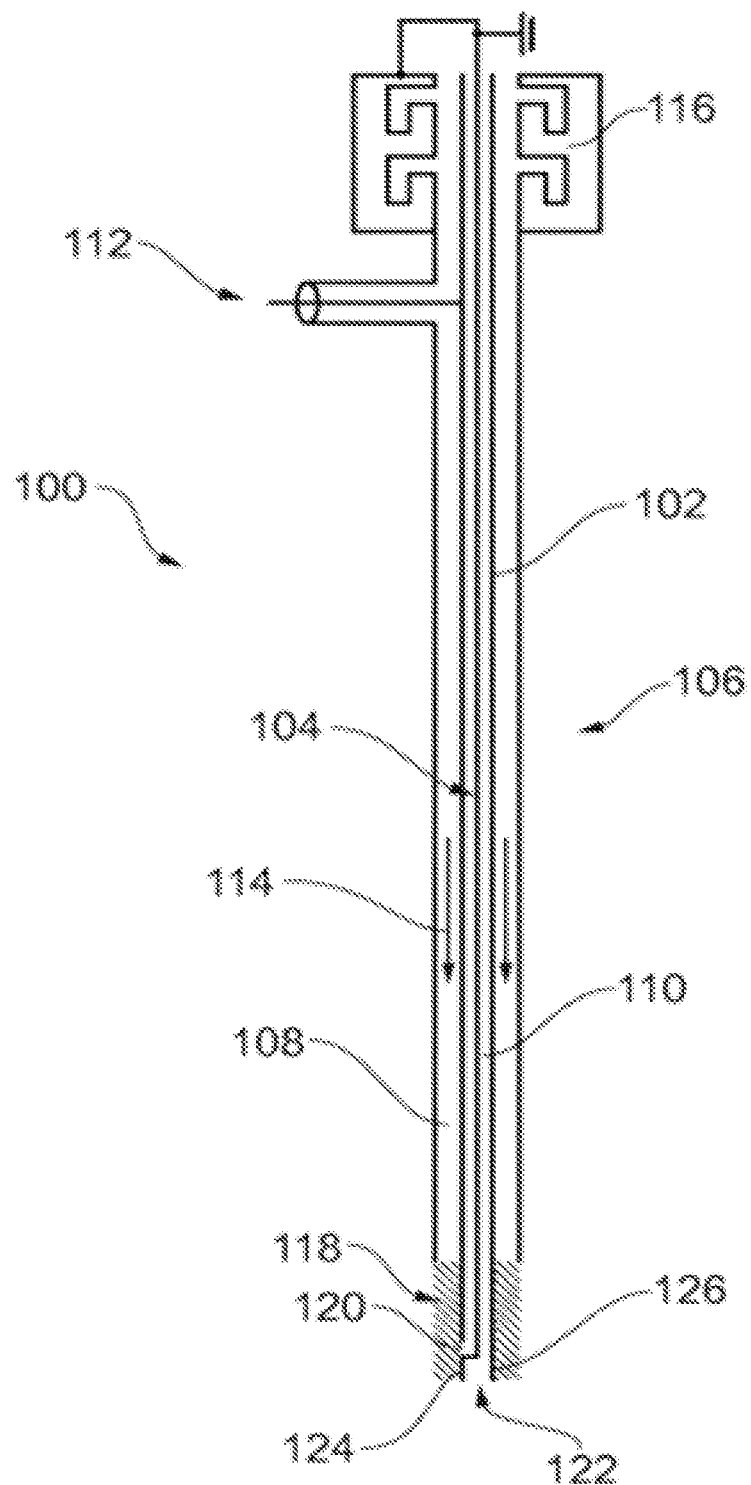
FIG. 1 is a schematic cross-sectional view of an energy conveying structure for a combined microwave ablation and RF resection electrosurgical instrument that is an embodiment of the invention.

FIG. 1 shows a schematic cross-sectional view of an energy conveying structure 100 according to the present invention. The energy conveying structure 100 is insertable in a flexible insertion tube of a surgical scoping device for invasive electrosurgery. The energy conveying structure 100 comprises a triaxial layered structure of multiple layers arranged coaxially relative to a longitudinal instrument axis that extends along the insertion tube.

The multi-layer coaxial structure may comprise an innermost dielectric layer (omitted from FIG. 1 for clarity) which is hollow to form an instrument channel 102 of the scoping device. An inner conductive layer 104 is formed on the innermost dielectric layer. An outer conductive layer 106 is formed coaxially with the inner conductive layer 104, with an intermediate dielectric layer 108 separating the inner conductive layer 104 and the outer conductive layer 106. The inner conductive layer 104, intermediate dielectric layer 108 and the outer conductive layer 106 form a first coaxial transmission line. According to an embodiment of the invention, within the instrument channel 102 there is an innermost conductive element 110, which in this embodiment is a thin metal wire or filament. The inner conductive layer 104, the innermost dielectric layer and the innermost conductive element 110 form a second coaxial transmission line.

At a proximal end of the energy conveying structure 100 there is a connector 112 for connecting the structure 100 to a generator (not shown). There may be an intermediate coaxial cable between the connector and the generator. The generator may be configured to generate radiofrequency (RF) and/or microwave energy which is conveyed by the multi-layer structure to a distal end of the energy conveying structure 100.

The first coaxial transmission line (e.g. formed by the inner conductive layer 104, the outer conductive layer 106 and the outer dielectric layer 108) may be arranged to convey microwave energy 114. The second coaxial transmission line (formed by the inner conductive layer 104, the innermost conductive element 110 and the innermost dielectric layer) may be arranged to convey conveying RF energy. The outer conductive layer 106 and the innermost conductive layer 110 are grounded, whereby the inner conductive layer is the signal conductor for both the first and second transmission lines. The second transmission line is thus inverted from a conventional coaxial structure, where the grounded conductor is normally outermost.

At the proximal end of the energy conveying structure 100 there is a diplexer 116 which acts both to connect the RF and microwave energy from the generator on to their respective transmission lines and also to prevent leakage over the signals between the transmission lines.

A radiator tip 118 made of ceramic material is positioned at the distalmost end of the energy conveying structure 100. The radiator tip 118 is a hollow cylinder which is positioned to be collinear with the outer dielectric later 108, and has the same inner and outer dimensions as the outer dielectric layer 108. The innermost conductive element 110, inner conductive layer 104 and inner dielectric layer are thereby able to extend through the radiator tip 118, but the outer conductive layer 106 terminates at or around the end of the outer dielectric layer 108. Due to this configuration, when microwave energy is conveyed along the structure 100, microwave energy is radiated from the tip 118 in a generally spherical pattern. This may produce microwave ablation in a generally spherical region of tissue.

The innermost conductive element 110 extends through the hollow interior of the radiator tip 118, and terminates at a return electrode 124 that is exposed at a distal end of the radiator tip 118. The return electrode may be radially displaced from the longitudinal axis of the device, whereby there is a step in the innermost conductive element 110 to make the necessary electrical connection. In one example, the return electrode is mounted on an inner surface of the passage through the radiator tip 118. The inner conductive layer 104 may include a distal extension that extends through the hollow interior of the radiator tip 118 to form an active electrode 126 that lies opposite the return electrode 124 at the distal end of the radiator tip. When RF energy is conveyed through the structure 100, an RF electric field is set up between the active electrode 126 and the return electrode 124 that enables cutting or resection may take place in a region 122 at the distal end of the radiator tip.

Figure 2:
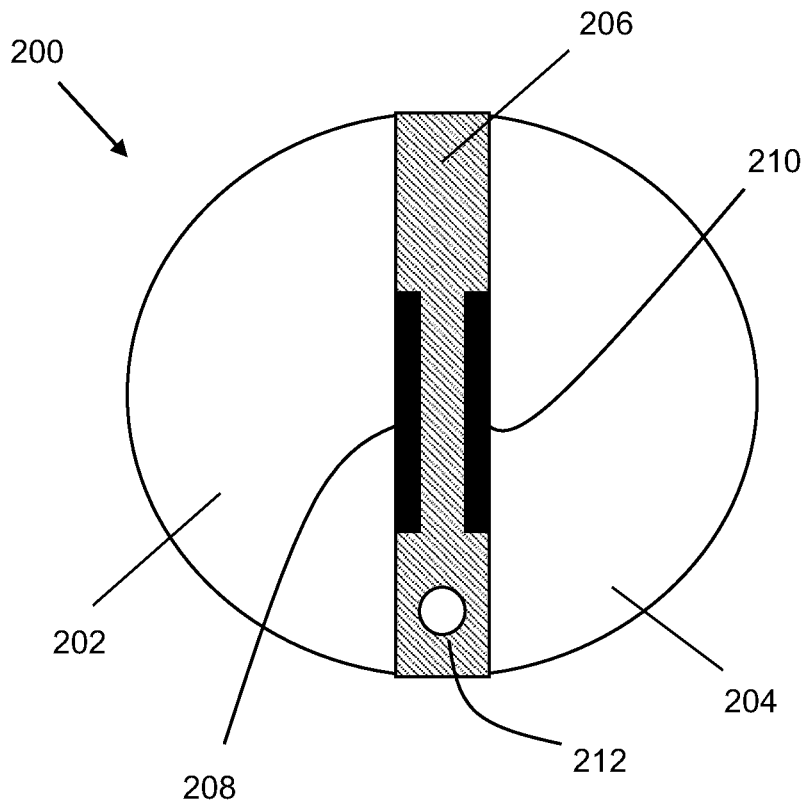
FIG. 2 is a schematic view of an alternative tip structure for a combined microwave ablation and RF resection electrosurgical instrument that is an embodiment of the invention.
Figure 2A:
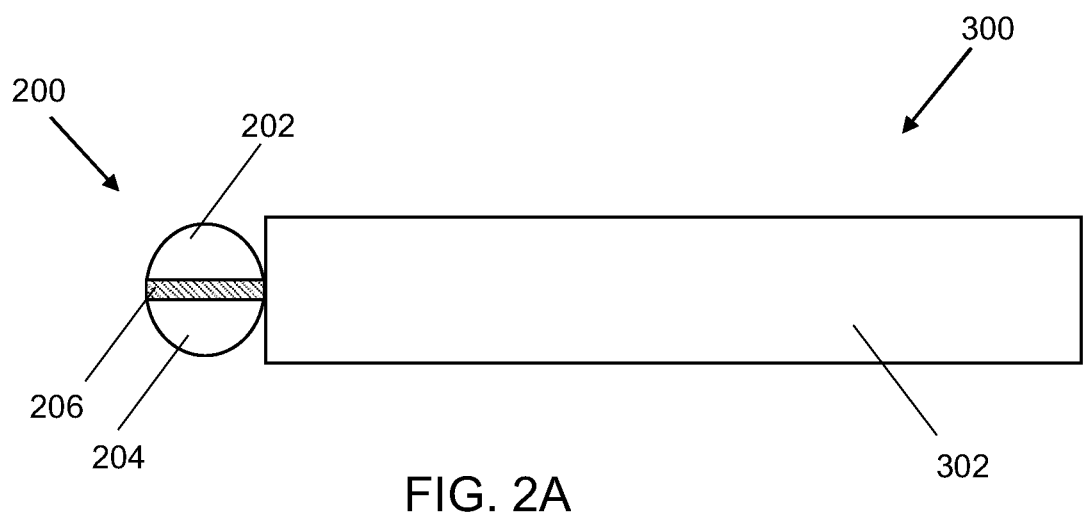

FIG. 2 is a schematic view of an alternative tip structure 200 for a combined microwave ablation and RF resection electrosurgical instrument that is an embodiment of the invention. The tip structure 200 comprises a substantially spherical radiator having a first hemisphere 202 and a second hemisphere 204, wherein the first hemisphere 202 and the second hemisphere 204 are each made of a conductive material. For example, each hemisphere may be made from a metallic material or shell. The first hemisphere 202 and the second hemisphere 204 are separated by a dielectric material 206 such that the first hemisphere 202, second hemisphere 204 and dielectric material 206 form a substantially spherical structure. The layer of dielectric material 206 may be less than 0.5 mm in thickness. A first electrode 208 is connected to an inner surface of the first hemisphere 202, and a second electrode 210 is connected to an inner surface of the second hemisphere 204. In this way, the first electrode 208 and the second electrode 210 oppose each other across the layer of dielectric material 206. The first electrode 208 and second electrode 210 cover at least a portion of the base of each respective hemisphere. In some embodiments, the first electrode 208 and second electrode 210 may cover substantially all of the base of each respective hemisphere.

The electrodes 208, 210 are respectively connected to the inner and outer conductors of a coaxial feed cable (not shown). In other embodiments, the electrodes 208, 210 may be omitted, and each hemisphere directed connected to a respective one of the inner and outer conductors. The coaxial feed cable is arranged to convey RF and microwave energy from a generator in the manner described above. The spherical tip structure shown in FIG. 2 may be dimensioned to fit within the instrument channel of a surgical scoping device.

The tip structure 200 is dimensioned to deliver the RF and microwave energy from the coaxial cable in different ways. At microwave frequencies, the separate hemispheres appear electrically like a single sphere. Microwave energy delivered to the tip structure 200 may thus be radiated by the first hemisphere 202 and the second hemisphere 204 in a substantially spherical pattern. In this way, the tip structure 200 is able to ablate a generally spherical region of tissue.

However, at radiofrequencies, the tip structure 200 appears electrically like a parallel plate capacitor. In this case, RF energy delivered to hemispheres sets up an RF field across the gap formed by the dielectric layer 206 that is capable of performing cutting or resection. Thus, the tip structure 200 is able to perform RF cutting and resection, where the resection is performed in the plane of the dielectric layer 206 and so can be controlled by movement of the instrument. For example, the instrument may be rotatable so that cutting is performed in a different plane.

The tip structure 200 may also be arranged to deliver fluid (e.g. saline or gas, e.g. to form a plasma for treatment). A fluid flow outlet 212 may be formed in the planar dielectric layer 206 to introduce fluid at the treatment site. The fluid flow outlet 212 may be in fluid communication with a fluid passageway in the coaxial feed cable. In some examples, the coaxial feed cable may comprise a hollow coaxial transmission line, i.e. a coaxial transmission line with a hollow inner conductor. The fluid passageway may be within the hollow inner conductor.

Figure 3A:
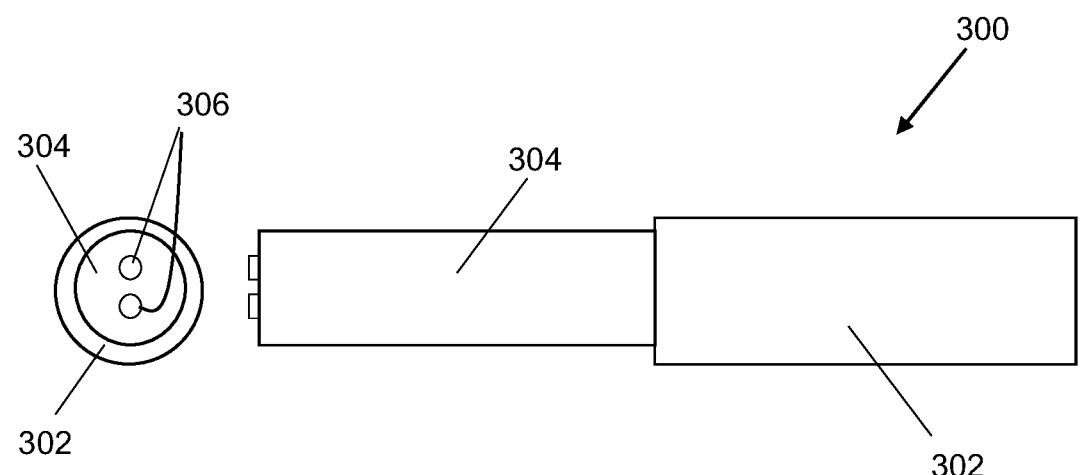
FIGS. 3A and 3B comprise a side view, a front and an axial cross-sectional of a tip structure for a combined microwave ablation and RF resection electrosurgical instrument that is another embodiment of the invention.
Figure 3B:
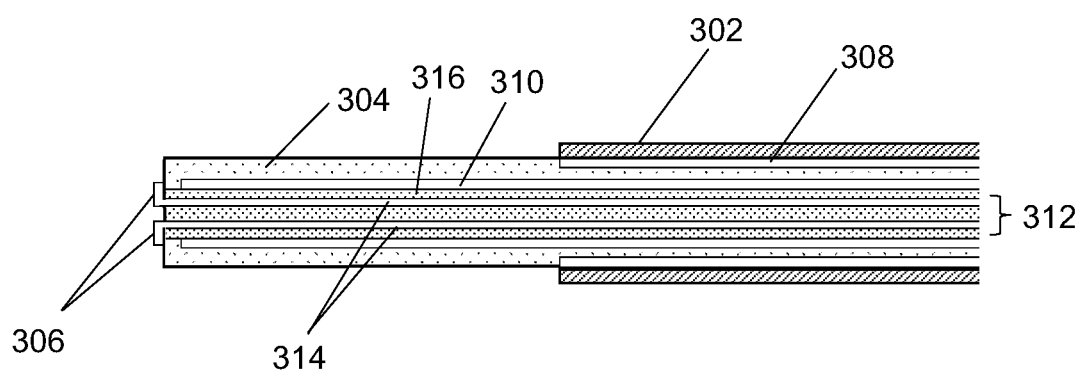

FIG. 3A shows a side view and front view of an electrosurgical instrument tip 300 that is another embodiment of the invention. FIG. 3B is a schematic cross-sectional view thereof. The instrument is configured as a coaxial transmission line comprises a hollow inner conductor 310 separated from an outer conductor 308 by an electrically insulating dielectric material 304. At a distal portion of the tip, the inner conductor 310 and dielectric material 304 protrude beyond a distal end of the outer conductor and a protective sleeve 302 to form a microwave antenna. Microwave energy delivered from a generator (not shown) at a proximal end of the coaxial cable can thus be emitted at the distal portion of the tip.

The hollow inner conductor 31 provides a channel 312 through which a pair of conductive wires 314 extend. The wires 314 terminate at their distal ends in a pair of electrodes 306 formed on the distal end face of the dielectric material 304. The wires 314 may form any suitable transmission line structure for conveyed radiofrequency (RF) energy, e.g. a twisted pair or the like. The wires may be embedded or encased in an electrically insulating sheath 316 that is conveyed through the channel 312. The pair of electrodes 306 are each connected to a respective wire 314 to form active and return electrodes for delivering RF energy. The electrodes 306 encourage a preferential current path for the RF energy across the distal face of the instrument tip to facilitate RF resection as the instrument is inserted through tissue.

The invention claimed is:

1. An electrosurgical instrument for delivering radiofrequency (RF) electromagnetic (EM) energy and microwave EM energy for resection and ablation of biological tissue, the instrument comprising:
   an energy conveying cable structure comprising:
     a coaxial transmission line for conveying microwave energy, the coaxial transmission line comprising an inner conductive layer, an outer conductive layer, and a dielectric layer separating the inner conductive layer from the outer conductive layer, wherein the inner conductive layer is formed around a hollow longitudinal passage along the cable structure; and a transmission line for conveying radiofrequency energy along the hollow longitudinal passage; and an instrument tip at a distal end of the energy conveying cable structure, the instrument tip comprising:

a dielectric tip element extending longitudinally beyond a distal end of an outer conductor, wherein an inner conductor extends longitudinally beyond the distal end of the outer conductor within the dielectric tip element to form a microwave radiator; and an active electrode and a return electrode mounted at a distal end of the dielectric tip element, wherein the active electrode and the return electrode are connected to the transmission line to support an RF field therebetween at the distal end of the dielectric tip element, wherein the coaxial transmission line for conveying the microwave energy is a first coaxial transmission line, and the transmission line for conveying the radiofrequency energy is a second coaxial transmission line, wherein the second coaxial transmission line comprises an innermost conductive element extending through the longitudinal passage, the inner conductive layer, and an innermost dielectric layer separating the inner conductive layer from the innermost conductive element, wherein the active electrode is electrically connected to the inner conductive layer and the return electrode is electrically connected to the innermost conductive element, and wherein the innermost conductive element and the outer conductive layer are configured to be electrically grounded during the delivery of each of the RF EM energy and the microwave EM energy, whereby the inner conductive layer is the signal conductor for both the first and second transmission lines.

2. The electrosurgical instrument according to claim 1, wherein the innermost conductive element is a conductive wire.

3. The electrosurgical instrument according to claim 1, wherein the innermost conductive element includes a control wire for manipulating the instrument tip.

4. The electrosurgical instrument according to claim 1, wherein the energy conveying cable structure is insertable through a flexible insertion tube of a surgical scoping device.

5. The electrosurgical instrument according to claim 1, wherein the energy conveying cable structure has an outer diameter equal to or less than 3 mm.

6. An electrosurgical apparatus comprising:
an electrosurgical generator arranged to supply radiofrequency energy and microwave energy; and
an electrosurgical instrument according to claim 1 connected to the electrosurgical generator, wherein the energy conveying cable structure is arranged to convey the microwave energy via the coaxial transmission line for conveying microwave energy and the radiofrequency energy via the transmission line for conveying radiofrequency energy.

7. An electrosurgical instrument for delivering radiofrequency (RF) electromagnetic (EM) energy and microwave EM energy for resection and ablation of biological tissue, the instrument comprising:
an energy conveying cable structure comprising:
a coaxial transmission line for conveying microwave energy, the coaxial transmission line comprising an inner conductive layer, an outer conductive layer and a dielectric layer separating the inner conductive layer from the outer conductive layer, wherein the inner conductive layer is formed around a hollow longitudinal passage along the cable structure; and a transmission line for conveying radiofrequency energy along the hollow longitudinal passage; and an instrument tip at a distal end of the energy conveying cable structure, the instrument tip comprising:

a dielectric tip element extending longitudinally beyond a distal end of an outer conductor, wherein an inner conductor extends longitudinally beyond the distal end of the outer conductor within the dielectric tip element to form a microwave radiator; and an active electrode and a return electrode mounted at a distal end of the dielectric tip element, wherein the active electrode and the return electrode are connected to the transmission line to support an RF field therebetween at the distal end of the dielectric tip element, wherein the transmission line for conveying the radiofrequency energy is a pair of wires extending through the hollow longitudinal passage, wherein the longitudinal passage extends through the dielectric tip element to provide a fluid flow path through the instrument.

8. The electrosurgical instrument according to claim 7, wherein the pair of wires are encased in an electrically insulating sheath.

9. An electrosurgical instrument for delivering radiofrequency RF) electromagnetic (EM) energy and microwave EM energy for resection and ablation of biological tissue, the instrument comprising:
an energy conveying cable structure comprising:
a coaxial transmission line for conveying microwave energy, the coaxial transmission line comprising an inner conductive layer, an outer conductive layer and a dielectric layer separating the inner conductive layer from the outer conductive layer, wherein the inner conductive layer is formed around a hollow longitudinal passage along the cable structure; and a transmission line for conveying radiofrequency energy along the hollow longitudinal passage; and an instrument tip at a distal end of the energy conveying cable structure, the instrument tip comprising:

a dielectric tip element extending longitudinally beyond a distal end of an outer conductor, wherein an inner conductor extends longitudinally beyond the distal end of the outer conductor within the dielectric tip element to form a microwave radiator; and an active electrode and a return electrode mounted at a distal end of the dielectric tip element, wherein the active electrode and the return electrode are connected to the transmission line to support an RF field therebetween at the distal end of the dielectric tip element, wherein the transmission line for conveying the radiofrequency energy is a pair of wires extending through the hollow longitudinal passage, wherein the dielectric tip element is ceramic.

10. An electrosurgical instrument for delivering radiofrequency (RF) electromagnetic (EM) energy and microwave EM energy for resection and ablation of biological tissue, the instrument comprising:
an energy conveying cable structure comprising:
a coaxial transmission line for conveying microwave energy, the coaxial transmission line comprising an inner conductive layer, an outer conductive layer and a dielectric layer separating the inner conductive layer from the outer conductive layer, wherein the inner conductive layer is formed around a hollow longitudinal passage along the cable structure; and a transmission line for conveying radiofrequency energy along the hollow longitudinal passage; and an instrument tip at a distal end of the energy conveying cable structure, the instrument tip comprising:

a dielectric tip element extending longitudinally beyond a distal end of an outer conductor, wherein an inner conductor extends longitudinally beyond the distal end of the outer conductor within the dielectric tip element to form a microwave radiator; and an active electrode and a return electrode mounted at a distal end of the dielectric tip element, wherein the active electrode and the return electrode are connected to the transmission line to support an RF field therebetween at the distal end of the dielectric tip element, wherein the transmission line for conveying the radiofrequency energy is a pair of wires extending through the hollow longitudinal passage;

wherein the electrosurgical instrument has a diplexer connected at a proximal end of the energy conveying cable structure.

11. An electrosurgical instrument for delivering radiofrequency (RF) electromagnetic (EM) energy and microwave EM energy for resection and ablation of biological tissue, the instrument comprising:

a coaxial transmission line for conveying the RF EM energy and the microwave EM energy, the coaxial transmission line comprising an inner conductive layer, an outer conductive layer and a dielectric layer separating the inner conductive layer from the outer conductive layer; and an instrument tip at a distal end of the energy conveying cable structure, the instrument tip comprising:

a first conductive hemisphere electrically connected to the inner conductive layer;

a second conductive hemisphere electrically connected to the outer conductive layer; and a planar dielectric layer located in a physical separation gap between the first conductive hemisphere and the second conductive hemisphere, wherein the first conductive hemisphere and the second conductive hemisphere are configured to: radiate the microwave EM energy as a substantially spherical field, and provide respectively an active electrode and a return electrode on opposing sides of the separation gap for delivering the RF EM energy, wherein the coaxial transmission line includes a fluid flow passage for conveying a fluid to the instrument tip.

12. The electrosurgical instrument according to claim 11, wherein the instrument tip has a diameter equal to or less than 3 mm.

13. The electrosurgical instrument according to claim 11, wherein the first conductive hemisphere and the second conductive hemisphere are symmetrically mounted on the planar dielectric layer.

14. The electrosurgical instrument according to claim 11, further including:

a first electrical connector mounted on a first surface of the planar dielectric layer, the first electrical connector electrically connecting the inner conductive layer to the first conductive hemisphere; and a second electrical connector mounted on a second surface of the planar dielectric layer opposite to the first surface, the second electrical connector electrically connecting the outer conductive layer to the second conductive hemisphere.

15. The electrosurgical instrument according to claim 11, wherein the instrument tip includes a fluid flow outlet connected to the fluid flow passage.

16. The electrosurgical instrument according to claim 15, wherein the fluid passage is through the planar dielectric layer.

* * * * *